United States Patent [19]

Hayashi et al.

[11] 4,402,227
[45] Sep. 6, 1983

[54] METHOD OF DETERMINING FATIGUE LIFE OF METALS

[75] Inventors: Makoto Hayashi; Shinji Sakata; Tasuku Shimizu, all of Hitachi, Japan

[73] Assignee: Hitachi, Ltd., Tokyo, Japan

[21] Appl. No.: 264,142

[22] Filed: May 15, 1981

[30] Foreign Application Priority Data

May 16, 1980 [JP] Japan .................................. 55/65499

[51] Int. Cl.³ ............................................. G01N 3/32
[52] U.S. Cl. ....................................... 73/812; 378/72
[58] Field of Search .................... 73/808, 812; 378/71, 378/72

[56] References Cited

U.S. PATENT DOCUMENTS 4,042,825  8/1977  Ruud ...................................... 378/72
4,287,416  9/1981  Kramer et al. ........................ 378/72

Primary Examiner—Jerry W. Myracle
Attorney, Agent, or Firm—Thomas E. Beall, Jr.

[57] ABSTRACT

A method of determining fatigue life of metals that are subject to the cyclic load. A metal that exhibits a half-value width that varies depending upon the degree of deformation by fatigue is melt-adhered onto a recessed portion formed in a metal of which the life is to be determined. The two metals are subjected to the cyclic load simultaneously. Then, the melt-adhered metal is irradiated with an X-ray, and a half-value width of an S-N curve of the resulting diffracted X-ray is measured, thereby to determine the fatigue life of the metal of which the life is to be estimated. The method is effective for accurately determining the life even for the metals which exhibit half-value widths that change very little depending upon the degree of deformation by fatigue.

8 Claims, 6 Drawing Figures

METHOD OF DETERMINING FATIGUE LIFE OF METALS

BACKGROUND OF THE INVENTION

The present invention relates to a method of determined fatigue life of metals, and specifically to a method of determining fatigue life by irradiating a metal that is subject to receive cyclic load with X-rays and by using a half-value width of a curve of diffracted X-ray intensity.

A conventional method of determining fatigue life of a metal relying upon the X-ray diffraction, consists of sticking a metal foil onto a portion that is to be measured, subjecting the metal foil to the fatigue together with the portion that is to be measured, and irradiating the metal foil with X-rays to determine the degree of fatigue of the portion that is to be measured based upon the width of integration of the resulting X-ray diffraction line. Alternatively the fatigue life is determined from a relation between the change in the residual stress and the change in a half-value width of the diffracted X-rays in the case of a carbon steel that is annealed or in the case of a material that is subjected to the machining by turning.

According to the former method of sticking the metal foil, however, it is difficult to detect the damage by fatigue of the portions where the metal foil cannot be stuck. Furthermore, it is difficult to so stick the metal foil that it is subjected to the fatigue to the same degree as the specimen that is to be measured, and to peel the metal foil from the specimen in such a manner that the damage by fatigue is not changed. The above-mentioned problems do not develop with the latter method by which the specimen is irradiated with the X-rays and an intensity curve of the diffracted X-rays is utilized. With the latter method, however, no change is recognized in the half-value width of the diffracted X-rays depending upon the processing method or the heat treatment, even when the specimen is deformed by fatigue. Namely, the damage by fatigue is not often detected, and the fatigue life is not accurately determined.

SUMMARY OF THE INVENTION

The present invention was accomplished in view of the above-mentioned problems. The object of the present invention therefore is to determine the fatigue life of any metal materials maintaining precision irrespective of the kind or the condition of the metal materials. Namely, according to the present invention, the life of the metal is indirectly determined by sputtering a metal onto a recessed portion that is formed by cutting a portion of a metal material that is to be measured, the sputtered metal exhibiting a half-value width of diffracted X-rays which changes depending upon the degree of deformation by fatigue, and by measuring the half-value width of the diffracted X-rays caused by the sputtered metal.

DETAILED DESCRIPTION OF THE PREFERRED EMBODIMENTS

Figure 2A:
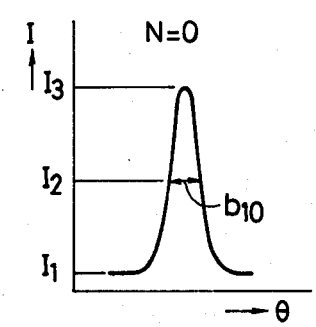
FIG. 2 shows curves for diffraction intensity versus the measurement angle of FIG. 1 for various cycle numbers.
Figure 2B:
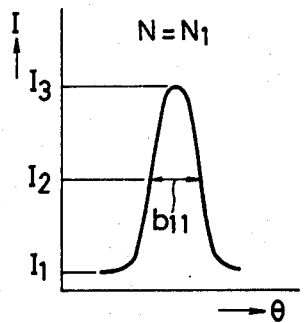
Figure 2C:
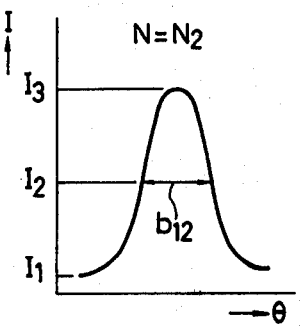
Figure 3A:
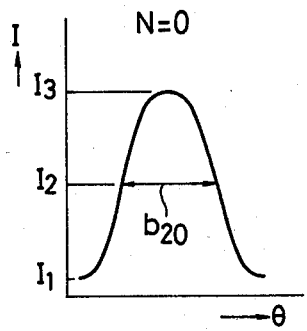
FIG. 3 shows a plurality of curves, similar to FIG. 2, but of the material after deformation.
Figure 3B:
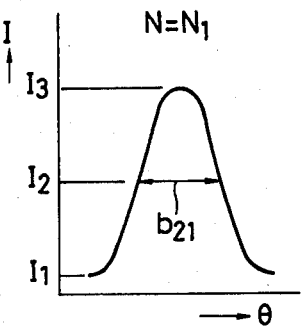
Figure 3C:
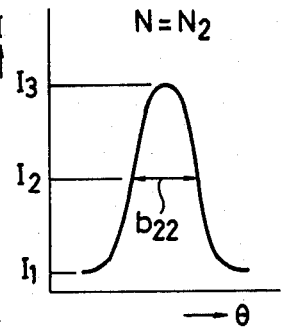

Below is mentioned how the half-value width of the diffracted X-ray which is obtained by irradiating a metal material with X-rays changes with the fatigue of the metal material, in conjunction with FIGS. 1 to 3.

Figure 1:
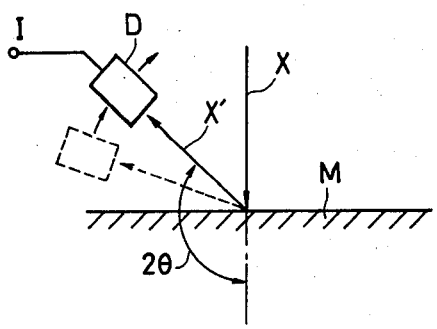
FIG. 1 schematically shows the physical arrangement for determining the fatigue life of a metal.

Referring to FIG. 1, a metal material M is irradiated with an X-ray X, and a diffracted X-ray X' which is diffracted in a direction of an angle $2\theta$ relative to the direction of irradiation is detected by a detector D. The detector D moves as diagrammatized to detect the diffracted X-ray X' at diffraction angles $2\theta$, and produces a signal of an X-ray diffraction intensity I. The X-ray diffraction intensity I changes as shown in FIGS. 2 and 3 if the stress line cycle number N to the metal material M is changed in a manner of $0 \rightarrow N_1 \rightarrow N_2$ ($0 < N_1 < N_2$). In this case, the half-value width b represents a width of diffraction angle having an X-ray diffraction strength which is greater than the X-ray diffraction intensity at $I_2 = (I_3 - I_1)/2$ (where $I_3$ denotes a peak value in the intensity and $I_1$ denotes a bottom value in the intensity). When the metal material M is annealed, the half-value width becomes as shown in FIG. 2. Namely, the half-value in the X-ray diffraction intensity I gradually increases with the increase in the fatigue. With the metal material M which is subjected to the plastic deformation, on the other hand, the half-value width in the X-ray diffraction intensity I gradually decreases with the increase in the fatigue as shown in FIG. 3.

Figure 4:
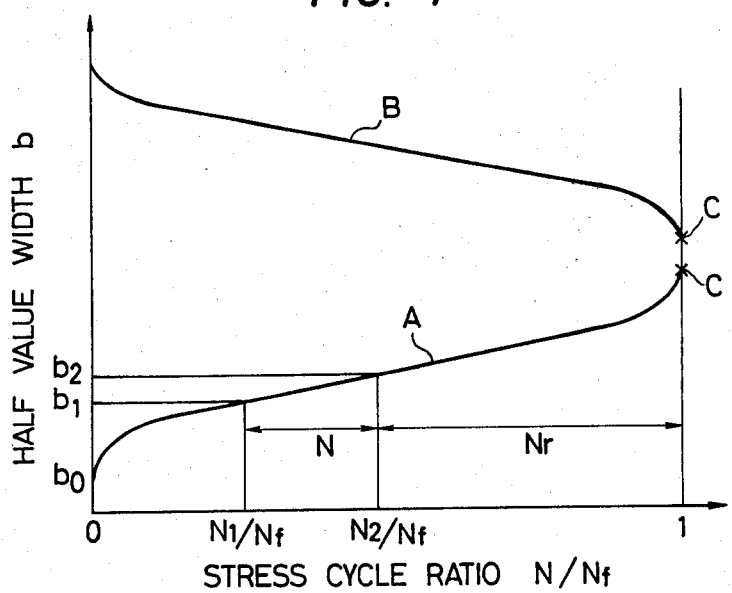
FIG. 4 shows curves of stress cycle ratio versus half-value width for an annealed material and a deformed material.

With reference to FIG. 4, the abscissa represents a stress cycle ratio $N/N_f$ (N denotes a stress cycle number and $N_f$ denotes a failure cycle number), and the ordinate represents a half-value width b during the process of getting fatigue. In FIG. 4, symbols $b_0$, $b_1$ and $b_2$ denote half-value widths when the stress line cycle number is 0, $N_1$ and $N_2$. A curve A represents an annealed material, a curve B represents a material that is subjected to the plastic deformation, points C denote failure points, and $N_r (= N_f - N)$ represents a remaining number of cycles from the moment of cycle number N to the failure point, i.e., represents a fatigue life (remaining life). As shown in FIG. 4, a relation between the stress cycle ratio and the half-value width is represented by a single line which is not dependent upon the stress amplitude even in the case of the annealed material or the plastically deformed material. Therefore, if a master curve which represents a relation between the stress cycle ratio and the half-value width is stored, the stress cycle ratio $N/N_f$ can be found from the master curve relying upon the measurement of the half-value width b of the metal material. Therefore, it is possible to readily find the remaining number of cycles from the number of cycles N at that moment to the failure point, i.e., to readily find the fatigue life $N_r$. When the number of cycles $N_1$ is not obvious, the material is subjected to the fatigue to a number of cycles $N_2 (N_2 - N_1 = N)$, and a half-value width $b_2$ is measured to find the fatigue life in accordance with the following relations. Namely, if it is regarded that the number N of stress cycles and the stress cycle ratio establish a proportional relation in FIG. 3, the fatigue life can be found from the following relation, $$\frac{N}{N_2/N_f - N_1/N_f} = \frac{N_r}{1 - N_2/N_f} \quad (1)$$

Therefore, the fatigue life $N_r$ is, $$N_r = \frac{N}{N_2/N_f - N_1/N_f} \cdot (1 - N_2/N_f) \quad (2)$$

where $N_1/N_f$ and $N_2/N_f$ are found by putting the measured half-value widths $b_1$ and $b_2$ on the master curve. It is further possible to find the remaining usable time by finding the time in which the material was used instead of finding the number N of cycles.

Figure 5:
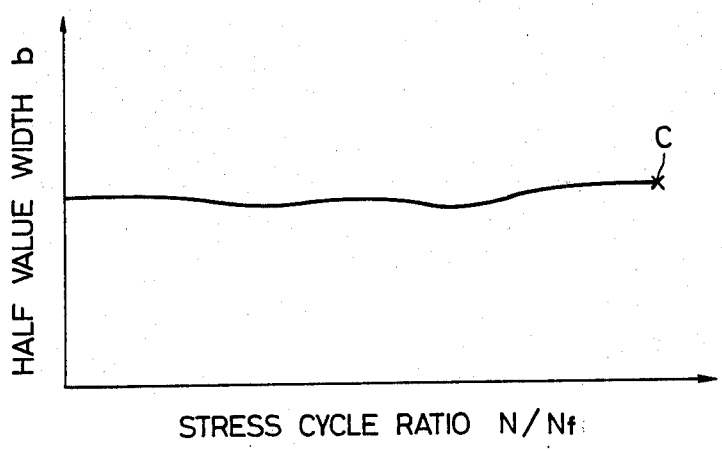
FIG. 5 shows a curve similar to that of FIG. 4, but of a different material.

The fatigue life is determined as mentioned above. Referring to FIG. 5, however, some materials exhibit a relation between the stress cycle ratio $N/N_f$ and the half-value width b, which changes very little. In the case of the materials which exhibit the half-value width b that changes very little, it is not possible to determine the fatigue life from the master curve. For example, cast steels such as chromium-molybdenum-vanadium steel and chromium-molybdenum steel exhibit a half-value width that changes very little, and make it difficult to determine the fatigue life.

Further, the metals used under high-temperature conditions or under corrosive conditions make it difficult to determine the fatigue life since their surfaces are covered with oxide scales or corrosion products.

According to the present invention, therefore, a metal which changes the half-value width depending upon the deformation by fatigue is attached to a portion of a structure that is to be measured, and the half-value width of the metal is measured to determine the fatigue of the structure that is to be measured. This method makes it possible to achieve the object which is contemplated by the present invention.

Figure 6:
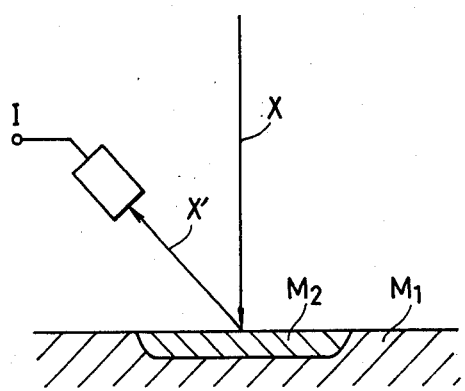
FIG. 6 is a schematic representation of the present invention.

The method of the present invention is illustrated below with reference to FIG. 6.

First, a recessed portion having a depth of 1 mm and an area of $1 \times 1$ mm$^2$ ($4 \times 4$ mm$^2$ in maximum area) is formed by machining in a portion of a structural member M$_1$ of which the fatigue life is to be measured, by using a milling machine or a grinder. Then, the recessed portion is filled with an acid-resistant and corrosion-resistant metal such as 25-chromium steel or SUS 304 by the welding method or by the plasma-welding method. Portions protruding beyond the surface of the structural member M$_1$ are removed. Thus, a metal M$_2$ is formed by the melt-adhesion. The surface of the melt-adhered metal M$_2$ which is filled in the recessed portion of the structural member M$_1$ is ground by an emery paper or a grinder to increase the half-value width, or is annealed by being heated by a gas burner or the like to decrease the half-value width. The stress cycle number N of the structural member or the time T in which it was used should be recorded prior to initiating the measurement by the detector D. After the diffracted X-ray X′ is measured by the detector D, the half-value width b of the melt-adhered metal M$_2$ is measured. Relying upon the master curve which has been recorded beforehand, the stress cycle ratio $N/N_f$ is found from the thus measured half-value width b, and the fatigue life $N_r$ is found from the relation (2) mentioned earlier.

Below is mentioned a relation of life between the melt-adhered metal 2 and the structural member 1. Materials used under high-temperature conditions are broken chiefly by the thermal stress which stems from the difference in the temperature distribution. The thermal stress can simply be given by $\epsilon = \beta \cdot \Delta T$ (where $\epsilon$ denotes strain, $\beta$ denotes a coefficient of linear expansion, and $\Delta T$ denotes a temperature difference). Therefore, the member 1 and the melt-adhered metal 2 are under the strain control. If a metallic material is subjected to the fatigue test to measure an S-N curve (stress—number of cycles), it will be recognized that the curve varies greatly depending upon the materials, manner of heat-treatment and manner of machining, in the case of the load control. According to the present invention which relies upon the strain control, however, the S-N curve (stress—number of cycles) varies very little even when the materials or the methods of heat-treatment and machining are changed. Therefore, the fatigue life of the melt-adhered test metal 2 can be regarded to be nearly equal to the fatigue life of the structural member 1. Consequently, the life measured from the melt-adhered metal 2 can directly be regarded as the life of the structural member 1.

The above-mentioned 25-chromium steel or SUS 304 having a coefficient of linear expansion $\beta$ which is greater than that of the structural member 1 will be used as the melt-adhered metal 2. Therefore, the melt-adhered metal 2 exhibits increased degree of fatigue, which means that the remaining life is determined modestly and the life of the structural members is determined on the safety side.

Under high-temperature atmosphere conditions, the materials undergo creep deformation. Here, the half-value width of the diffracted X-ray increases with the increase in the creep deformation. Therefore, it is also possible to detect the damage by creep and to determine the fatigue life.

As mentioned above, the method of determining fatigue life of metals according to the present invention, makes it possible to determine the fatigue life maintaining precision irrespective of the kind of the metals that are to be measured or irrespective of the conditions in which the metals to be measured are placed. Accordingly, the method of the present invention gives great industrial advantages.

What is claimed is:

1. A method of determining the fatigue life of a subject metal, comprising:
    forming a recessed portion in the subject metal of which the fatigue life is to be determined;
    melt-adhering a test metal into said recessed portion, said test metal exhibiting a half-value width which varies depending upon the degree of deformation by fatigue and having a residual fatigue life nearly equal to the subject metal;
    subjecting the metal-adhering test metal together with the subject metal to fatigue;
    thereafter detecting a diffracted X-ray which is obtained when said melt-adhered test metal is irradiated with an X-ray;
    finding the half-value width of X-ray diffraction relying upon the diffracted X-ray which is detected;
    comparing said half-value width with a fixed reference half-value width versus stress cycle characteristic of said test metal; and determining the fatigue life of said subject metal from said comparing.

2. A method of determining fatigue life of metals according to claim 1, wherein the melt-adhered test metal is annealed or is plastically deformed before it is irradiated with the X-ray.

3. A method of determining fatigue life of metals according to claim 1, wherein the melt-adhered test metal is composed of an acid-resistant metal or a corrosion-resistant metal.

4. The method of claim 1, wherein said step of forming a recess forms the recess to a depth of about 1 millimeter and for an area having orthogonal dimensions within the range of 1 millimeter to 4 millimeters; and
 further including the step of removing excess melt-adhered test metal that extends outwardly from the subject metal beyond the former surface contour of said subject metal in said area that existed prior to said step of forming.

5. A method of determining the fatigue life of a subject metal, comprising:
 forming a recessed portion in the subject metal of which the fatigue is to be determined;
 melt-adhering a test metal into said recessed portion, said test metal exhibiting a half-value width which varies depending upon the degree of deformation by fatigue and having a residual fatigue life nearly equal to the subject metal;
 subjecting said subject metal and adhered test metal to fatigue;
 thereafter detecting a diffracted X-ray which is obtained when said melt-adhered test metal is irradiated within an X-ray;
 finding the half-value width of X-ray diffraction relying upon the diffracted X-ray which is detected;
 comparing said half-value width with a fixed reference half-value width versus stress cycle ratio characteristic of said test metal; and
 determining the fatigue life of said subject metal relying upon said comparing between the half-value width and the stress cycle ratio of said melt-adhered test metal.

6. A method of determining the fatigue life of metals according to claim 5, wherein the melt-adhered metal is annealed or is plastically deformed before it is irradiated with the X-ray.

7. A method of determining the fatigue life of metals according to claim 5, wherein the melt-adhered metal is an acid-resistant metal or a corrosion-resistant metal.

8. The method of claim 5, wherein said step of forming a recess forms the recess to a depth of about 1 millimeter and for an area having orthogonal dimensions within the range of 1 millimeter to 4 millimeters; and
 further including the step of removing excess melt-adhered test metal that extends outwardly from the subject metal beyond the former surface contour of said subject metal in said area that existed prior to said step of forming.

* * * * *